United States Patent [19]
Bergamaschi

[11] Patent Number: 5,411,892
[45] Date of Patent: May 2, 1995

[54] METHOD AND APPARATUS FOR CARBOHYDRATE ANALYSIS

[75] Inventor: Brian A. Bergamaschi, Seattle, Wash.

[73] Assignee: University of Washington, Seattle, Wash.

[21] Appl. No.: 106,060

[22] Filed: Aug. 13, 1993

[51] Int. Cl.$^6$ .......................................... G01N 33/66
[52] U.S. Cl. ..................... 436/94; 436/161; 536/18.5; 536/22.1; 536/124; 536/123.1
[58] Field of Search ................... 436/93–95, 436/161; 536/18, 22, 18.5, 18.6, 22, 124; 435/6

[56] References Cited

U.S. PATENT DOCUMENTS

| | | | |
|---|---|---|---|
| 4,607,125 | 8/1986 | Mott | 568/319 |
| 4,736,022 | 4/1988 | Rademacher et al. | 536/22 |
| 4,965,400 | 10/1990 | Vicari et al. | 560/130 |
| 4,990,681 | 2/1991 | Curtis et al. | 568/324 |

FOREIGN PATENT DOCUMENTS

| | | | |
|---|---|---|---|
| 0215351 | 3/1987 | European Pat. Off. | C07C 45/46 |
| 4021001 | 1/1992 | Germany | C07H 13/04 |

OTHER PUBLICATIONS

Lipniunas, P. et al. "Mass Spectrometry of High-Mannose Oligosaccharides after Trifluoroacetolysis and Periodate Oxidation". Anal. Biochem. 200, 58–67 (1994).

Defaye J. et al. "The Behavior of Cellulose, Amylose, and B-D-XYLAN Towards Anhydrous Hydrogen Fluoride." Carbohydrate Research 110 (1982) 217–227.

Knirel et al., "Application of Anhydrous Hydrogen Fluoride for the Structural Analysis of Polysaccharides", *Advances in Carbohydrate Chemistry and Biochemistry* (47)(1989), pp. 167–203.

Miethchen et al., "From Isopropylidene Sugars to Acylated Pyranosyl or Furanosyl Fluorides in One Step", *Synthesis* (10), (1991) pp. 885–888, Abstract Only.

Mietchen et al., "From Isopropylidene Sugars to Acylated Pyranosyl or Furanosyl Fluorides in One Step", *Synthesis* (10), (1991) pp. 885–888.

*Primary Examiner*—David A. Redding
*Attorney, Agent, or Firm*—Christensen, O'Connor, Johnson & Kindness

[57] ABSTRACT

A method for analyzing carbohydrates involves solvolyzing the carbohydrate in anhydrous hydrogen fluoride. Solvolysis is terminated by the introduction of a carboxylic acid anhydride to the solvolyzed carbohydrate and hydrogen fluoride reaction mixture, resulting in the formation of acetic acid and acetic acid acyl fluoride. The acetic acid acyl fluoride reacts with hydroxyl groups on the solvolyzed carbohydrate to form peracylated carbohydrates. The resulting peracylated carbohydrates are dried to remove the solvent by-products, and can then be separated by gas chromatography. The gas chromatography eluents are then identified using mass spectrometer. An apparatus for automatically carrying out the solvolysis and carboxylic acid anhydride termination and acetylization steps is also provided.

25 Claims, 4 Drawing Sheets

METHOD AND APPARATUS FOR CARBOHYDRATE ANALYSIS

GOVERNMENT RIGHTS IN THE INVENTION

This invention was made with government support under Grant #OCE-9101908 awarded by the National Science Foundation. The government has certain rights in the invention.

FIELD OF THE INVENTION

The present invention relates to the field of carbohydrate analysis, and more particularly to the solvolysis of polysaccharides into constituent oligosaccharides and monosaccharide moieties to allow characterization of the polysaccharide.

BACKGROUND OF THE INVENTION

The ability to analyze carbohydrates is becoming increasingly important in a variety of fields. Environmental studies often require the analysis of geochemical samples that include a complex mixture of carbohydrates. Concern over fossil fuel emissions and corresponding increases in the atmospheric carbon dioxide concentrations have stimulated study of the global carbon cycle, the geologic cycle that ultimately determines the atmospheric concentration of carbon dioxide. The response time of the carbon cycle to increased atmospheric carbon dioxide depends in large measure on the rate of preservation of detrital plant material in marine sediments. Marine sediments include a complex mixture of organic and mineral materials, including significant quantities of carbohydrates. The study of carbohydrates in geochemical samples is thus an important aspect of the study of carbon cycling.

The ability to characterize carbohydrates is also of significant importance in analytical biochemistry, and in particular to the relatively new field of glycobiology. Additional applications for carbohydrate analysis include the food sciences, biomass utilization and pulp and paper chemistry fields.

Current methods for carbohydrate analysis are complex, labor intensive and can be inaccurate. Conventional chemical methods of analysis typically include hydrolysis of the polymeric carbohydrates, i.e., polysaccharides, into the corresponding oligosaccharides and monosaccharides. These constituents can then be quantified by a variety of methods, including gas and liquid chromatography. However, the intrinsic reactivity of carbohydrates in the analytical media during hydrolysis often results in adverse reactions of the hydrolyzed mono and oligosaccharides. These reactions occur under the same conditions as required for hydrolysis. Thus, for example, during analysis of carbohydrates in marine sediments, hydrolysis may be coupled with extra-molecular condensation reactions occurring with other compounds present in the sediment, and intermolecular reactions involving rearrangements or eliminations of the saccharide moieties.

A recent improvement to conventional methods of carbohydrate depolymerization involves solvolysis in hydrogen fluoride. Solvolysis of polymeric hydrocarbons results in cleavage of glycoside linkages to form glycosyl fluorides. Hydrogen fluoride is an ideal solvolysis agent, in that solvolysis of carbohydrates that are resistant to other methods can be readily accomplished. Additionally, solvolysis with hydrogen fluoride does not result in significant decomposition of the constituent sugars, and does not affect any N-acyl substituents of acylamido sugars that may be present. Under certain conditions, O-acyl substituents that are present can also be retained. Once a carbohydrate is solvolyzed with hydrogen fluoride, the resultant glycosyl fluoride is rapidly equilibrated with oxocarbenium ion due to the stability of such ions in this medium.

Conventional methods of hydrogen fluoride solvolysis are summarized in a review article by Knirel, U.A. et al., "Application of Anhydrous Hydrogen Fluoride for the Structural Analysis of Polysaccharides," *Advances in Carbohydrate Chemistry and Biochemistry*, 47:167-202 (1989), the disclosure of which is hereby expressly incorporated by reference. However, such conventional methods have limitations associated with termination of the solvolysis reaction.

One conventional method for terminating the hydrogen fluoride solvolysis reaction is the removal of hydrogen fluoride by evaporation m vacuo. This purging of the hydrogen fluoride often results in repolymerization of the solvolyzed carbohydrate. The solvolyzed mono- and oligosaccharides undergo cross-reactions, resulting in the formation of new secondary oligosaccharides.

Other conventional methods of terminating the hydrogen fluoride solvolysis reaction involve neutralization with a suspension of calcium carbonate and dichloromethane, or precipitation with cold ether. These methods also may involve undesirable cross-reactions. The variable solubility of carbohydrates, including charged ionic carbohydrates, in ether also results in this method being less accurate than desired.

Techniques have also been developed for utilizing a solvolysis mixture of hydrogen fluoride and methanol to prepare methyl glycosides of sugars. However, when a relatively high ratio of methanol to hydrogen fluoride is utilized, the removal of the solvents from the resulting mixture by evaporation is difficult. (Knirel et al. at 174).

SUMMARY OF THE INVENTION

The present invention provides a method for analyzing carbohydrates, including the steps of: solvolyzing the carbohydrate in anhydrous hydrogen fluoride; and reacting the solvolyzed carbohydrate and hydrogen fluoride reaction mixture with a carboxylic acid arthydride to form acylated carbohydrates. The acylated carbohydrates may then be quantified using known analytical techniques, which may include gas chromatography and mass spectrometry.

In a further aspect of the present invention, an apparatus is provided for automatically analyzing carbohydrates. The apparatus includes a first reagent reservoir resistant to hydrogen fluoride, a second reagent reservoir, and at least one reaction vessel that is resistant to hydrogen fluoride, for containing a polymeric carbohydrate analyte. The apparatus further includes a supply mechanism for sequentially supplying hydrogen fluoride from the first reagent reservoir and acetic anhydride from the second reagent reservoir to the reaction vessel, wherein the supply mechanism is resistant to hydrogen fluoride. The apparatus further includes a controller for automatically controlling the supply means to: (i) supply hydrogen fluoride from the first reagent reservoir to the reaction vessel; (ii) followed by a reaction delay to permit the solvolysis of the polymeric carbohydrate analyte; (iii) followed by supply of acetic arthydride from the reaction reservoir to the reaction vessel.

The present invention provides a method and automated apparatus for analyzing carbohydrates using hydrogen fluoride solvolysis while avoiding many of the undesirable cross-reactions associated with conventional hydrogen fluoride solvolysis methods. Termination of the sololysis reaction with acetic anhydride in accordance with the present invention results in quenching the solvolysis, removal of the hydrogen fluoride by chemical consumption, and simultaneous derivatization to stabilize the depolymerized carbohydrate.

By controlling specific reagents included in the reaction scheme, as discussed below, and the temperature of the reaction, the resulting monosaccharide and oligosaccharides can be controlled with specificity. The reaction products obtained can selectively include glycosyl fluorides, methyl glycosides and glycosyl acetates. The present invention also enables analysis of carbohydrates that are often difficult to handle using conventional methods. For example, simultaneous analysis of both acidic and basic sugars is possible. The hydrolysis efficiency afforded by the present invention has been found to be in excess of 85% for difficult to hydrolyze polymers such as chitin.

BRIEF DESCRIPTION OF THE DRAWINGS

The present invention and many of its attendant advantages will be better understood in view of the following description, when read in conjunction with the accompanying drawings in which.

DETAILED DESCRIPTION OF THE PREFERRED EMBODIMENT

Figure 1:
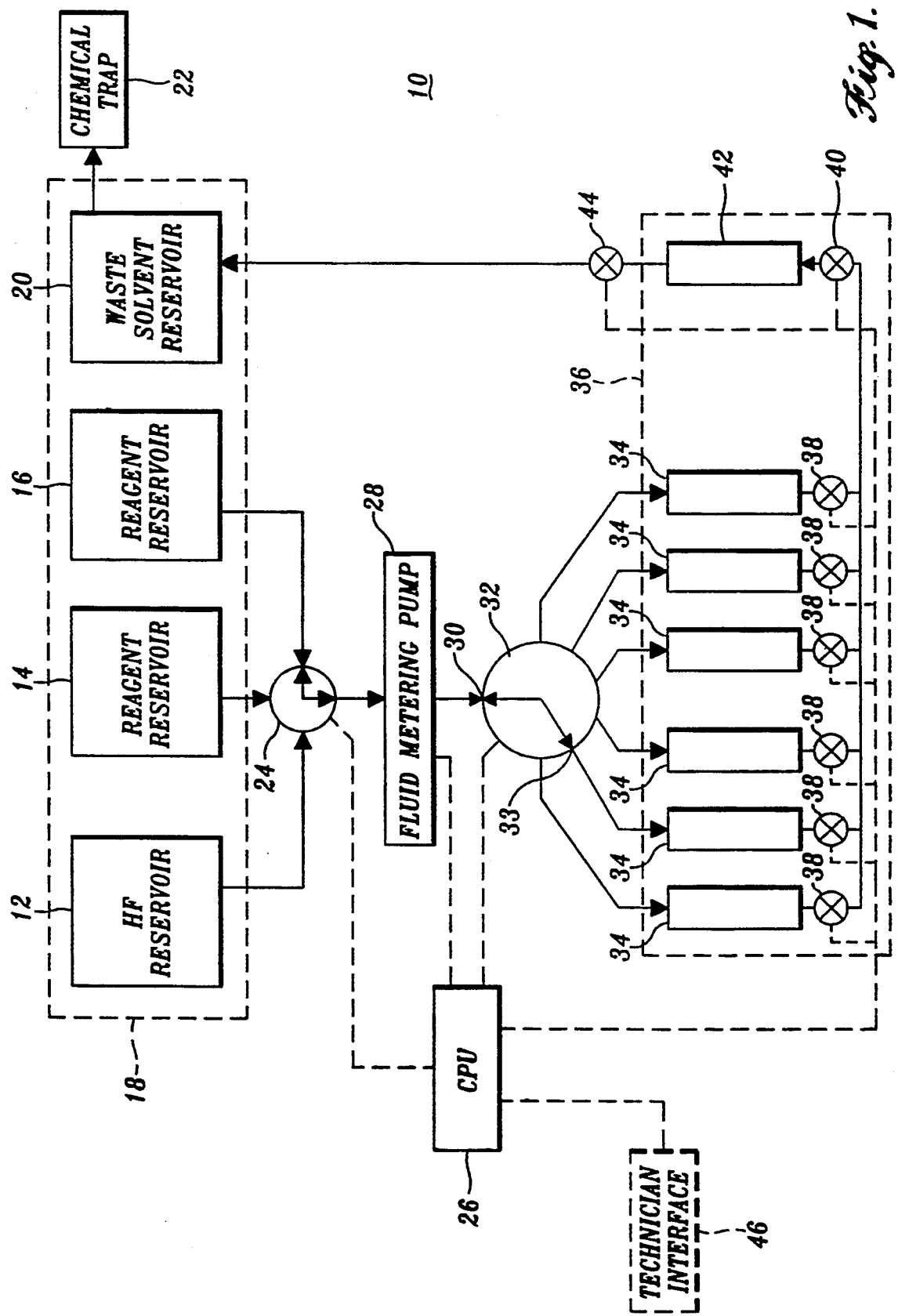
FIG. 1 is a schematic diagram of a sequential-sample automated carbohydrate analyzer constructed in accordance with the present invention.

The present invention provides a method for analyzing carbohydrates, which begins with the step of solvolyzing the carbohydrate in anhydrous hydrogen fluoride. The glycosidic linkages of the carbohydrate are cleaved, yielding depolymerized glycosyl fluorides in a hydrogen fluoride solution. Acetic anhydride is then added to this solution to terminate the solvolysis, i.e., eliminate hydrogen fluoride by consumption while simultaneously derivatizing the glycosyl fluorides to yield peracylated carbohydrate monomers and oligomers. These reaction products can then be dried, followed by quantitative and/or qualitative analysis.

The present invention is useful for analyzing a broad range of carbohydrates, e.g., polysaccharides, including as a non-limiting list of examples starches, cellulose, xylans, amylose, chitin, inulin, pectin, agar, carageenan and natural gums. Acetic and basic carbohydrates, as well as carbohydrates that are typically resistant to hydrolysis, may be analyzed.

The method entails the initial step of solvolyzing the carbohydrate analyte in anhydrous hydrogen fluoride. The carbohydrate analyte is added to prepare a dilute solution. For example, the inventor has found the addition of 0.5 to 2 mg of carbohydrate analyte to a 0.5 ml quantity of hydrogen fluoride to be suitable. Solvolysis is carried out at a pressure ranging from atmospheric to an enhanced pressure as high as 40 pounds per square inch. These conditions are preferred due to maintain the highly toxic and corrosive hydrogen fluoride (boiling point 19.5° C.) as a liquid.

Solvolysis results in cleavage of the glycoside carbohydrate linkages, while the ring structures remain intact so that condensation reactions are avoided. Fluorine from the hydrogen fluoride enables formation of highly stable glycosyl fluorides that are not subject to rearrangement or condensation, as long as the solution remains dilute.

The temperature and time of the reaction is controlled to obtain the desired degree of depolymerization. Higher temperatures or times generally result in complete depolymerization while lower temperatures or times result in the production of oligosaccharides, while still lower temperatures or times result in the production of larger oligosaccharides. Preferably, temperature is maintained at from 40° to 25° C. By controlling the solvolysis conditions, a carbohydrate analyte may be obtained that is small enough to be characterized to deduce the structure of the source carbohydrate while still retaining sufficient polymerization. The solvolysis reaction is carried out for a period typically of from one to tbur hours, dependent in part on the temperature, but may be extended to 24 hours or longer.

While the preferred embodiment of the present invention utilizes anhydrous hydrogen fluoride as the solvolysis agent, other mineral acids may be suitable for use. For example, hydrogen chloride may be suitable for practice of the present invention. However, because hydrogen chloride vaporizes at a much lower temperature, hydrogen fluoride is preferred to simplify, handling.

After solvolysis has occurred for the desired time, solvolysis is terminated by the addition of an acylation agent to the solution of depolymerized carbohydrate in hydrogen fluoride. The acylation agent is preferably a carboxylic acid anhydride, more preferably a lower alkyl acid anhydride, and still more preferably a $C_1$–$C_6$ alkyl carboxylic acid anhydride. The most preferred acylation agent is acetic anhydride. However, other carboxylic acid anhydrides are also suitable for use in the present invention, including benzoic acid anhydride. The acetic anhydride serves to chemically eliminate the hydrogen fluoride and also to derivatize the depolymerized carbohydrate to a stable form. At least an equimolar of acetic anhydride, and preferably an excess of acetic anhydride (relative to the molar amount of hydrogen fluoride) is added directly to the hydrogen fluoride reaction mixture. Most preferably, at least two times equimolar excess of acetic anhydride is used.

A significant advantage of the method of the present invention resides in the fact that the hydrogen fluoride need not be evaporated or otherwise removed from the reaction mixture prior to addition of the acetic anhydride. The acetic anhydride reacts with the hydrogen fluoride, yielding acetic acid and acetyl fluoride, i.e., acetic acid acyl fluoride. The acetyl fluoride then reacts with the depolymerized carbohydrates to form peracylated carbohydrates, which are readily analyzed using gas chromatography. Thus, the addition of acetic arthydride serves to quench the solvolysis reaction, and also serves to remove the hydrogen fluoride chemically, rather than by evaporation as required in many conventional methods. As well as chemically consuming the hydrogen fluoride, the addition of acetic arthydride also results in the simultaneous derivatization of the solvolyzed carbohydrate analytes to form the peracylated carbohydrates, with consequent stabilization of the carbohydrate.

Because of the heat of reaction of the acetic anhydride with the hydrogen fluoride reaction mixture, one or both are preferably cooled prior to the addition. Preferably, the hydrogen fluoride reaction mixture is cooled to a temperature between −60° C. to 0° C., and the acetic anhydride is cooled to a temperature between −80° C. and room temperature. The acetic anhydride is added rapidly to the hydrogen fluoride reaction mixture, preferably in a pressure vessel.

After termination of the solvolysis reaction by the addition of the acetic anhydride, the resulting peracylated carbohydrate products are preferably dried under reduced pressure to remove the solvent by-products. In particular, a vacuum may be utilized to remove acetyl fluoride, acetic acid, and any remaining excess acetic anhydride through evaporation by differential volatility. For example, the inventor has found a vacuum of approximately 500 millitorr suitable to dry the carbohydrate products. A dry gas stream is also suitable tier removal of the solvents.

The highly reactive acetyl fluoride is readily removed by evaporation. Additionally, because acetic acid is more volatile than acetic anhydride, the acetic acid is removed prior to the acetic anhydride, thereby preventing concentration of the carbohydrates in the acid during evaporation, and further preventing undesirable cross-reactions. Because of the stability of the peracylated carbohydrates, and the differential volatility of the solvent by-products, no deacetylization is evidenced during the drying step. After drying, no other clean up of the derivatized alkalytes is required.

The dried carbohydrate derivatives can be further analyzed quantitatively and/or qualitatively to identify the derivatized carbohydrates, and thereby hopefully also identify the source carbohydrates, using conventional techniques. These include gas chromatography and mass spectrometry. For example, the inventor has found the use of gas chromatography to separate the derivatized carbohydrates, followed by mass spectrometry, useful in characterizing the products and source carbohydrates. Prior to introduction to the gas chromatograph, the derivatized carbohydrate products are suspended in a solvent that is readily volatized in the gas chromatograph and yet is inert to the products, such as pyridine. Other solvents, such a chloroform, can alternately be used. The eluent from the gas chromatograph can then be supplied to a mass spectrometer to quantify and further identify the peracylated carbohydrate derivative products.

Practice of the present invention results in a solvolysis efficiency in excess of 85%. Recover efficiency of the carbohydrates has been found to be in excess of 99%. The method of the present invention has been found useful for analyzing a variety of carbohydrates that are difficult to hydrolyze, such as highly crystalline carbohydrates, including cellulose. The present invention also affords the ability to analyze mixtures of both acidic and basic carbohydrates. Thus, the present invention is well suited for analyzing complex mixtures of carbohydrates, such as are obtained from marine sediments. Acetyl groups from any N-acetyl glucosamine in the samples are not affected, because the acetyl groups are not cleaved off by the hydrogen fluoride.

As discussed above, the exact carbohydrate derivatives obtained through practice of the present invention can be controlled by controlling the reaction temperature. Additionally, further reagents may be utilized to further selectively control the derivatives produced. For example, the formation of peracylated carbohydrate derivatives can be enhanced by the addition or production of acetic anhydride during a portion of the solvolysis reaction, followed by heating to an elevated temperature. The analyte carbohydrate is first solvolyzed in hydrogen fluoride in accordance with the method set forth above. A preferably equimolar (relative to the hydrogen fluoride) amount of acetic acid is then added to the hydrogen fluoride reaction mixture, the reaction mixture is heated to above ambient temperature, and solvolysis is continued. Preferably, the reaction mixture is heated to a temperature of approximately 80° C., and maintained for a period of approximately 1 hour. After this time, an excess of acetic anhydride is added to quench the solvolysis reaction.

Alternately, instead of adding the equimolar acetic acid, the yield of peracylated derivative can be increased in a similar fashion by altering the termination step. After solvolysis of the carbohydrate polymer in hydrogen fluoride as set forth in the basic reaction scheme above, an equimolar quantity of acetic anhydride is added to the reaction mixture to quench the solvolysis, followed by heating of the quenched reaction mixture to an elevated temperature of approximately 80° C., for a period of approximately 1 hour. This encourages the formation of acetic acid, and thus the formation of the pentaacetate carbohydrate derivative.

As a further example of varying the reaction scheme to control the derivatives formed, dry methanol can be added to the reaction mixture after hydrogen fluoride solvolysis and before the addition of acetic anhydride. Thus, after hydrogen fluoride solvolysis in accordance with the method set forth above, dry methanol or another nucleophile is added to the hydrogen fluoride reaction mixture. Preferably, sufficient methanol is added to make a 6.0 molar solution of hydrogen fluoride in methanol. This reaction mixture is allowed to react tier a period of time of from 15 minutes to 24 hours, yielding methyl glycoside instead of glycosyl fluoride. An excess of acetic anhydride is then added to quench the reaction mixture. Sufficient excess acetic anhydride must be added to account For the termination of acetic acid methyl ester. Any excess methanol is later removed during the drying step as the acetic acid methyl ester.

In some cases, after acetylizing the solvolyzed carbohydrate analyte, it may be desirable to add t-butyl alcohol or toluene prior to drying the derivatized product, to further inhibit cross-reactions. However, the peracylated carbohydrate derivatives have been found sufficiently stable that this is typically not required.

While the above method has been described as useful for analyzing carbohydrates, it should also be appreciated by one of ordinary skill in the art that the solvolysis and termination steps of the present invention could be carried out as a precursor in a carbohydrate synthesis scheme, particularly to specifically glcosylate other compounds or to synthesize oligomeric carbohydrates. This method may also have utility for glycosylating proteins.

Because the method of the present invention described above utilizes all liquid constituents, it can be used in a novel automated analytical apparatus of the present invention. FIG. 1 provides a schematic illustration of an automated analytical apparatus 10 for practice of the method of the present invention. The apparatus 10 is preferably integrated within a housing (not shown). All reagents are fully contained within the apparatus during use, to prevent exposure of the reagents to the analytical technician and the atmosphere.

The apparatus 10 includes a first fluid reservoir 12 for use in containing hydrogen fluoride. The first fluid reservoir 12 and all other components within the apparatus 10 that come into contact with the hydrogen fluoride are constructed from a material that is resistant to hydrogen fluoride, such as a fluorinated plastic, e.g., polytetrafluoroethylene, or a high nickel stainless, e.g., T3-16. The apparatus 10 also includes at least one reagent reservoir 14 for containing the acetic anhydride. The apparatus 10 may further include at least one additional reagent reservoir 16 for containing reagents, such as methanol or acetic acid, for use with the method variations described previously. The reagent reservoirs 12, 14 and 16 are housed within a temperature-controlled compartment 18 to enable cooling of the reagents. The temperature-controlled compartment 18 also includes a waste solvent reservoir 20 that exhausts to a chemical vapor trap 22.

Flow of fluids from the reagent reservoirs 12, 14 and 16 are controlled by a reagent selector valve 24 that can be selectively actuated to select positions enabling flow from the desired reagent reservoir 12, 14, 16 or to prevent flow from any of the reagent reservoirs. Operation of the reagent selector valve 12 is automatically controlled by a central processing unit 26 contained within the apparatus 10.

When the reagent selector valve 24 is set to a desired position to permit flow from a corresponding reagent reservoir 12, 14 or 16, fluid passes through the reagent selector valve 24 to a fluid metering pump 28. The fluid metering pump 28 may be any of several conventional pump designs, such as a syringe pump or a diaphragm pump. Output from the fluid metering pump 28 is supplied to the inlet port 30 of a distribution valve 32. The distribution valve 32 has a selectively positionable outlet port 33. The fluid metering pump 28 and distribution valve 32 are also controlled by the central processing unit 26. A plurality of sample vials 34 are housed within a second temperature-controlled chamber 36 of the apparatus 10. Each sample vial 34 serves as a pressure reaction vessel for the solvolysis of a carbohydrate analyte contained therein. The temperature of the temperature-controlled chambers 18 and 36 is automatically maintained at a desired level, as controlled by the central processing unit 26.

The distribution valve 32 can be sequenced through a series of positions to position tile outlet port 33 of the distribution valve to permit reagent flow to a mating inlet port of a selected sample vial 34. Suitable multi-position distribution valves are available for liquid chromatograph applications. When the outlet port 33 is positioned to place the distribution valve 32 in fluid communication with a particular sample vial 34, reagent from one of the reagent reservoirs 12, 14 or 16 is permitted to flow into the selected sample vial 34.

Each sample vial 34 also includes an outlet port, from which fluid flow is permitted or prevented by operation of a corresponding valve 38, controlled by the central processing unit 26. This permits adjustment of pressure within the sample vials 34, with excess fluid being exhausted through the valves 38 to the inlet valve 40 of a pressurized solvent trap 42. The solvent trap 42 is also housed within the second temperature-controlled chamber 36. A valve 44 on the outlet of the solvent trap 42 controls flow of fluid from the solvent trap 42 to the waste solvent reservoir 20. The valves 40 and 44 are also controlled by the central processing unit 26.

For use of the apparatus 10, as many carbohydrate analyte samples as are desired to be analyzed are manually loaded within corresponding sample vials 34. Sample vials 34 are then installed into the second temperature-controlled chamber 36, and connected in fluid flow communication between the distribution valve 32 and the outlet valves 38. Each sample vial 34 serves as a pressurized reaction vessel, and can be maintained at a desired temperature by controlling the temperature within the chamber 36.

Once the loaded sample vials 34 are placed within the apparatus 10, the technician performing the analysis activates operation of the apparatus 10 by entering an appropriate command on a technician interface 46, such as a keyboard. The interface 46 communicates with the central processing unit 26, which then operates the valves 24, 32, 38, 40, and 44, as well as the fluid metering pump 28, to automatically perform the solvolysis and derivatization of the analyte carbohydrates in the sample vials 34.

The apparatus 10 of FIG. 1 is set up to introduce reagents sequentially to each of the sample vials 34. The reagents within the first chamber 18 are precooled to reaction temperature. The reagent selector valve 24 is initially positioned to permit flow from the first reagent reservoir 12, which contains hydrogen fluoride, to the fluid metering pump 28. The fluid metering pump 28 is operated to cause flow of hydrogen fluoride through the reagent selector valve 24 to the distribution valve 32. The fluid distribution valve 32 is positioned by the central processing unit 26 to permit flow to a first of the sample vials 34. Hydrogen fluoride is thus introduced into the first sample vial 34. When flow has been maintained for an adequate time predetermined to allow introduction of the desired quantity of hydrogen fluoride, the distribution valve 32 is sequenced to permit flow of hydrogen fluoride to the next sequential sample vial 34. This is repeated until hydrogen fluoride has been added to each of the sample vials 34.

Solvolysis of the carbohydrate analyte and hydrogen fluoride is then permitted to occur for the desired length of time, with temperature being controlled within the second temperature-controlled chamber 36. After the hydrogen fluoride has been added to each of the sample vials 34, the reagent selector valves 24 and distribution valves 32 are positioned to prevent flow between the first reagent reservoir 12 and the sample vials 34, and the fluid metering pump 28 can be deactivated. Further reagent flow is thus delayed during this period of time.

After solvolysis has been completed for the desired period of time, the reagent selector valve 24 is positioned to permit flow from the second reagent reservoir 14, containing the acetic anhydride. The acetic anhydride is then introduced sequentially to each of the sample vials 34, in the same manner in which the hydrogen fluoride was introduced. The solvolysis reaction is thus terminated, and the solvolyzed carbohydrates are derivatized within the reaction chambers formed by the sample vials 34. In between these steps, if the addition of other reagents such as methanol is desired, such reagent is introduced to each of the sample vials 34 by appropriately adjusting the reagent selector valve 24 for fluid communication with the reagent reservoir 16. While three reagent reservoirs 12, 14, and 16 have been shown in the apparatus 10, it should be readily apparent that additional reagent reservoirs can be added as required to accommodate the desired reaction scheme.

Whenever adjustment of pressure within tile sample vials 34 is required for further addition of fluids, the valves 38 and 40 can be operated to allow exhaust into the solvent trap 42. The valves 38 and 40 are then closed, and the waste solvent can be exhausted through the valve 44 to the waste solvent reservoir 20.

When the appropriate reagents have been added and the solvolysis and derivatization reactions are complete, the system is depressurized and the sample vials 34 can be removed from the apparatus 10. The derivatized samples are then preferably dried and introduced to further analytical equipment, such as a gas chromatograph and mass spectrometer.

Figure 2:
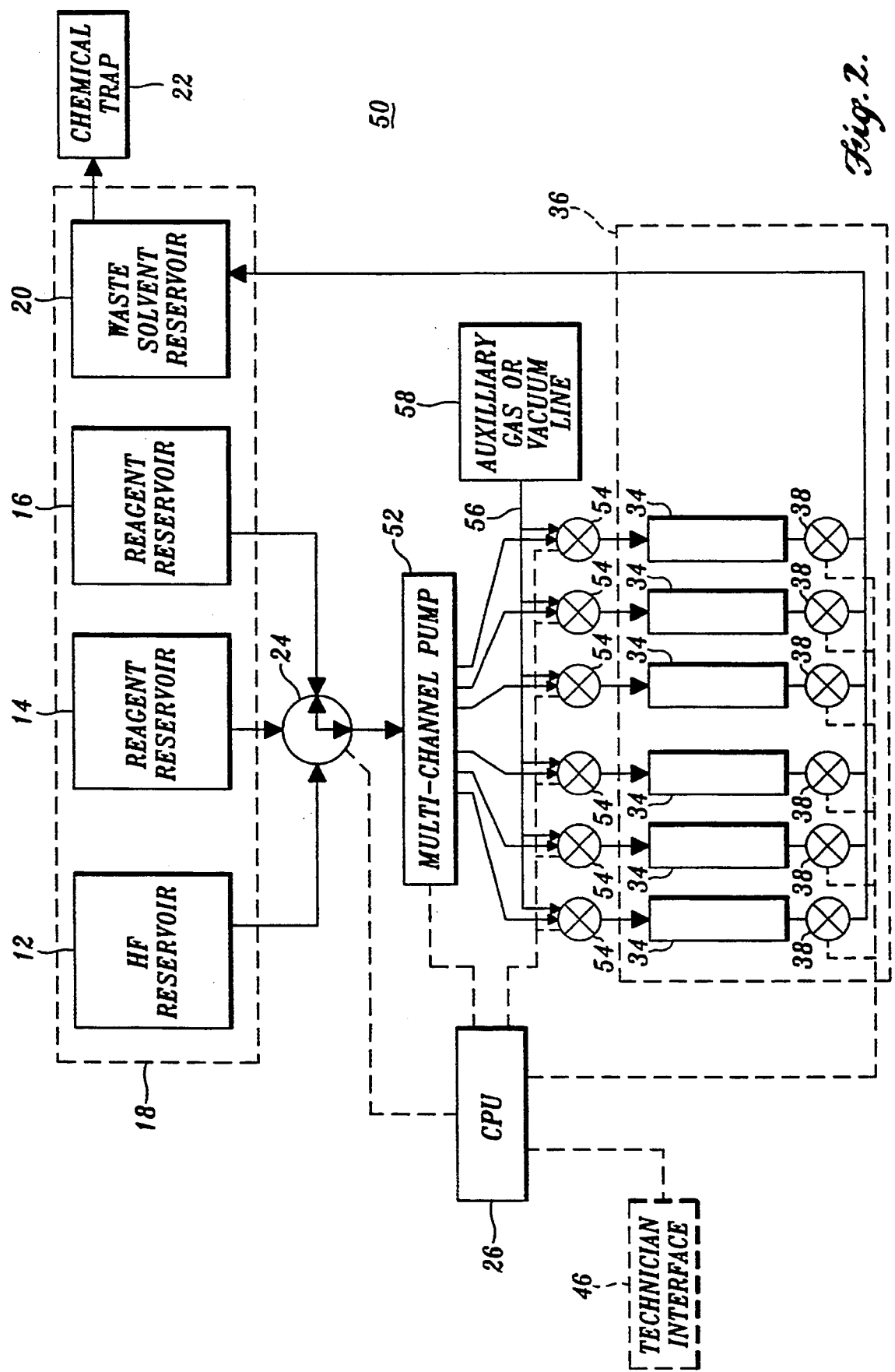
FIG. 2 is a schematic diagram of a multi-channel automated carbohydrate analyzer constructed in accordance with the present invention.

An alternate version of an automated analytical apparatus 50 constructed in accordance with the present invention is shown in FIG. 2. The apparatus 50 is identically constructed to the previously described apparatus 10, with several exceptions to be noted. Those components which are in common with the apparatus 10 are thus referred to with the same identifying numbers, and description of such common features is foregone to avoid redundancy. The apparatus 50 permits multichannel introduction of reagents to the individual analyte carbohydrate samples within the sample vials 34. This is effected through utilization of a multi-channel pump 52 in place of the fluid metering pump 28 and distribution valve 32 used in the apparatus 10.

When the reagent selector valve 24 is positioned to permit flow from a selected reagent reservoir 12, 14, or 16, such reagent flows simultaneously to each of the solvent vials 34 through corresponding inlet valves 54. The inlet valves 54 are also controlled by the central processing unit 26. To permit adjustment of pressure within the sample vials 34, each inlet valve 54 to a corresponding sample valve 34 is connected to an auxiliary gas line 56 that is in fluid communication with a source 58 of pressure or vacuum. The apparatus 50 is thus more efficient to use than the apparatus 10, because reagents can be added simultaneously to each of a desired number of sample vials 34. Operation of the apparatus 50 is otherwise similar to operation of the apparatus 10, described previously.

EXAMPLE 1

Figure 3:
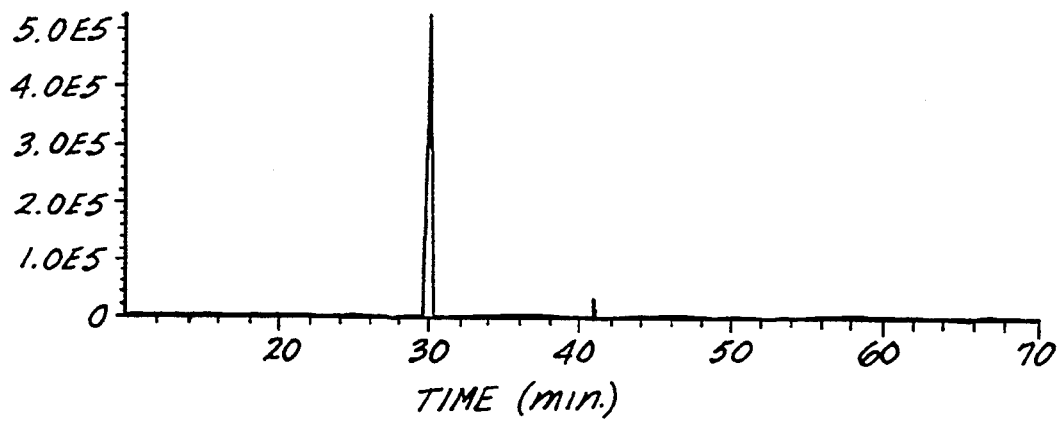
FIGS. 3, 4, 5, 6, 7 and 8 are graphs showing the output from a mass spectrometer, with total ion abundance represented on the y axis versus time in minutes on the x axis, produced from analysis of the reaction products obtained from solvolyzing carbohydrates in accordance with the present invention, as set forth in Examples 1, 2, 3, 6, 7, and 8, respectively, with the reaction products having been separated by gas chromatography prior to analysis with the mass spectrometer.

0.5 ml of anhydrous hydrogen fluoride was added to approximately 1.8 mg of 1-O-Methyl glucopyranose contained within a reaction vessel that had been precooled to 0° C. Solvolysis was carried out for two hours, with the temperature of the reaction mixture being maintained at 25° C. Solvolysis was then terminated by the addition of 18 ml of cold ($-60°$ C.) acetic anhydride. The resulting solution was then dried under reduced pressure to remove acetic acid, acetyl fluoride and any excess acetic anhydride. The dried solution was then resuspended in pyridine. A sample of this solution was then injected into a Hewlett-Packard Model 5890 series gas chromatograph, using a J.W. Scientific Model. DB1701 column. The eluant from the gas chromatograph was introduced into a Hewlett-Packard Model 59970 mass spectrometer, having a 70 Evionization potential. As shown in the total ion chromatogram of FIG. 3, a major product having an elution time of 30 minutes was obtained, and was identified as 1-fluoro glucose tetraacetate. A minor product having an elution time of approximately 40.5 minutes was found and identified as glucose pentaacetate.

EXAMPLE 2

Figure 4:
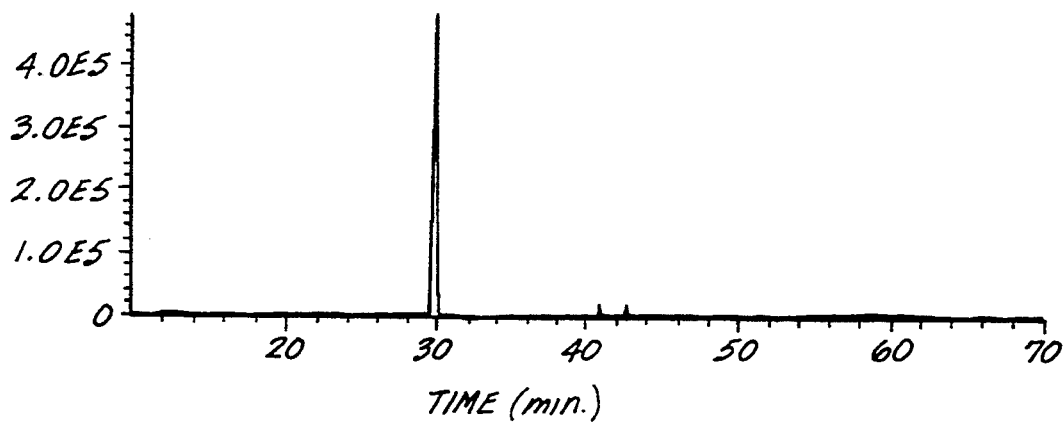

The same procedure as set forth in Example 1 was followed, except that the anhydrous hydrogen fluoride was introduced to 1.6 mg of the 1-O-Methyl glucopyranose and the solvolysis reaction was terminated by the addition of slightly more than an equimolar amount of acetic anhydride in a 50:50 V/V mixture of acetic anhydride and diethyl ether. The diethyl ether is an inert solvent in the reaction scheme. As shown in the total ion chromatogram of FIG. 4, the same products as produced in Example 1 were identified, with an additional peak at approximately 41.5 minutes identified as a contaminant.

EXAMPLE 3

Figure 5:
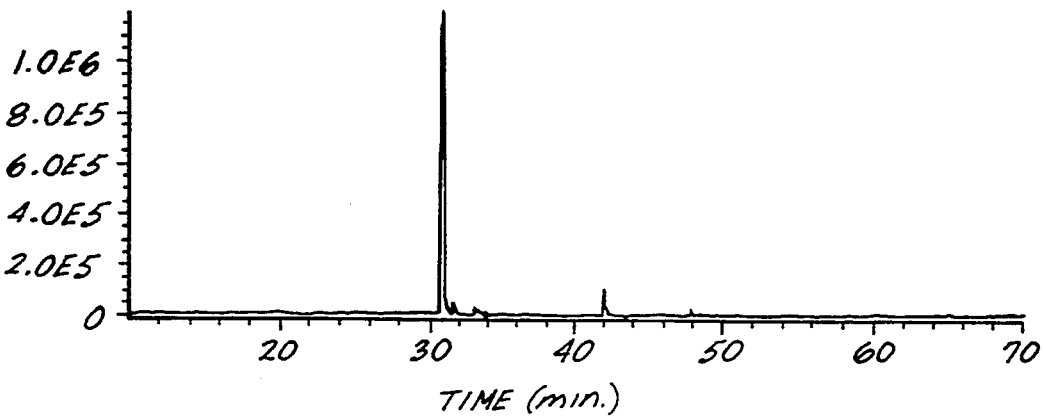

Approximately 1.6 mg of cellulose was solvolyzed in anhydrous hydrogen fluoride at 0° C. for two hours, followed by termination by the addition of excess acetic anhydride, using the procedure as otherwise set forth in Example 1. A major reaction product again was found to be 1-fluoro glucose tetraacetate, with a minor reaction product of glucose pentaacetate, as shown in the total ion chromatogram of FIG. 5.

EXAMPLE 4

Approximately 1 mg of cellulose was solvolyzed in anhydrous hydrogen fluoride for two hours at 0° C., following the procedure of Example 3, with the exception of the method of termination. Solvolysis was terminated by quenching with an equimolar (relative to the anhydrous hydrogen fluoride) amount of acetic anhydride. This quenched reaction mixture was then heated to 80° C. and maintained at that temperature for one hour, to encourage the formation of acetic acid. The resulting products were dried and analyzed as in Example 1. The heating of the reaction mixture after quenching with acetic anhydride was found to encourage formation of the pentaacetate. Analysis by gas chromatography and mass spectrometry, using the procedure of Example 1, showed the major reaction product to be glucose pentaacetate, and the minor reaction product to be 1-fluoro glucose tetraacetate.

EXAMPLE 5

The procedure of Example 3 was followed, except after solvolysis in hydrogen fluoride, an equimolar amount of acetic acid (relative to the hydrogen fluoride) was added, and solvolysis was continued for an additional hour at 80° C. Solvolysis was then terminated by the addition of an excess of acetic anhydride. The resulting product was dried and analyzed as set forth in Example 1. The addition of acetic anhydride and heating before termination also was found to result in the production of a greater quantity of pentaacetate. The major reaction product was again found to be glucose pentaacetate, with a minor reaction product of 1-fluoro glucose tetraacetate also found.

EXAMPLE 6

Approximately 1.6 mg of 1-O-Methyl glucopyranose was solvolyzed in anhydrous hydrogen fluoride at 25°

Figure 6:
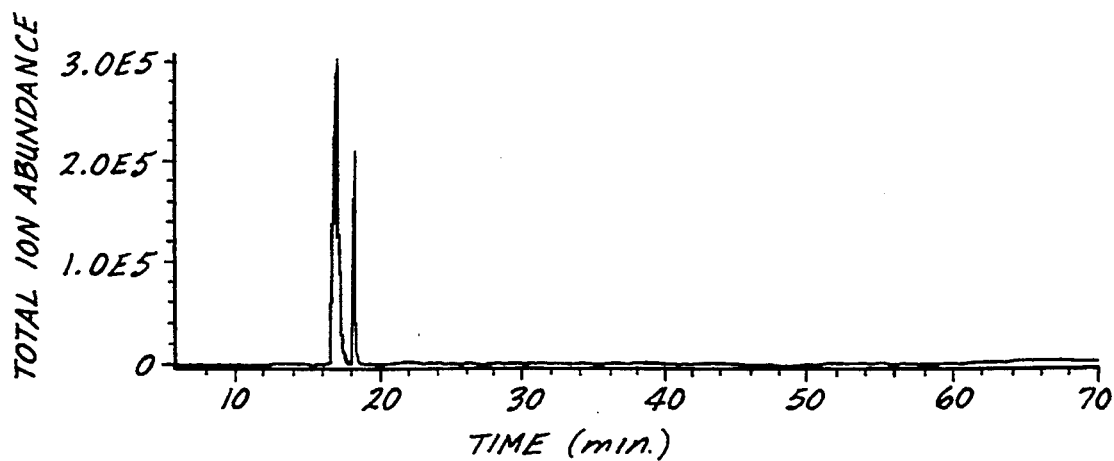

C. for 1 hour, following the procedure of Example 1 except as otherwise noted. Prior to termination, the solution was cooled to 0° C. and sufficient dry methanol was added to form a solution of 4.0 molar hydrogen fluoride in methanol. The solvolysis reaction was allowed to continue for 8 additional hours at 25° C. This methanolysis reaction was then terminated by the addition of cold (−75° C.) acetic anhydride. After drying in accordance with the procedure of Example 1, the products were resuspended in a 50:50 v/v solution of pyridine and acetic anhydride, and heated to 100° C. for 1 hour to assure complete acetylation. After redrying and gas chromatography and mass spectrometry in accordance with Example 1, the resulting products were found to be α- and β-Methyl glycosides, as shown in the total ion chromatogram of FIG. 6.

EXAMPLE 7

Figure 7:
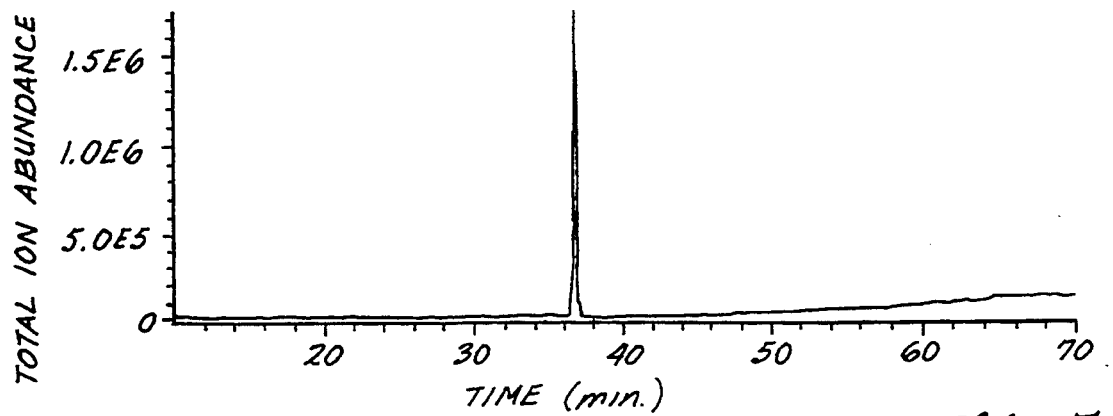

Approximately 2.0 mg of unpurified crab shell chitin, a polymer of N-acetyl glucosamine, was solvolyzed in anhydrous hydrogen fluoride at 0° C. for 4 hours, otherwise in accordance with the procedure of Example 1. Solvolysis was terminated by the addition of an excess of acetic anhydride, and the product was dried and analyzed in accordance with the procedure of Example 1. As shown in the total ion chromatogram of FIG. 7, the resulting product was found to be 1-fluoroglucosamine tetraacetate.

EXAMPLE 8

Figure 8:
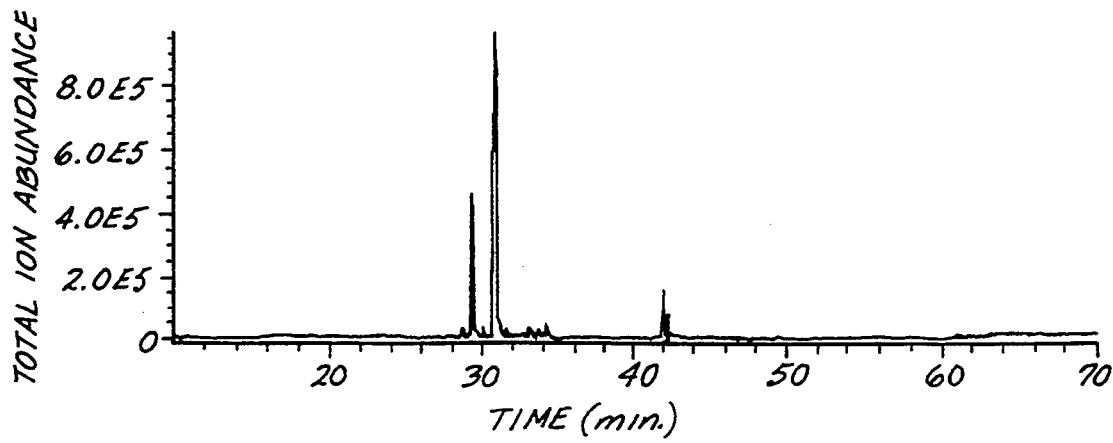

Approximately 1.3 mg. of unpurified xanthan gum, a polymer of glucose, mannose, and glucuronic acid, was solvolyzed in anhydrous hydrogen fluoride at 0° C. for 3 hours. In accordance with the procedure of Example 1, solvolysis was terminated by the addition of an excess of acetic anhydride, followed by drying, gas chromatography and mass spectrometry analysis. As shown in the total ion chromatogram of FIG. 8, the resulting products correspond to 1-fluoro-glucose tetraacetate, 1-fluoro-mannose pentaacetate and 1-fluoro-glucuronic acid tetraacetate. Mannose and glucose derivatives coelute under these conditions.

The present invention has been described in terms of several preferred embodiments and examples. However, various alterations, modifications and substitutions can be made by one of original) skill in the art, based on the disclosure contained herein. It is therefore intended that the scope of letters patent granted hereon by limited only by the definitions contained in the appended claims and equivalents thereto.

The embodiments of the invention in which an exclusive property or privilege is claimed are defined as follows:

1. A method for analyzing polymeric carbohydrates, comprising the steps of:
    (a) solvolyzing a polymeric carbohydrate in anhydrous hydrogen fluoride to yield a solution of at least partially depolymerized carbohydrate;
    (b) terminating the solvolysis by reacting the solution of at least partially depolymerized carbohydrate in the hydrogen fluoride with a carboxylic acid anhydride to form acylated carbohydrates; and
    (c) analyzing the qualitative or quantitative identity of the acylated carbohydrates as an indication of the type and structure of the carbohydrates present prior to solvolysis.

2. The method of claim 1, wherein the step of solvolyzing includes controlling the temperature of the polymeric carbohydrate and hydrogen fluoride during solvolysis at a selected temperature of from −40° to 20° C.

3. The method of claim 1, wherein the step of terminating the solvolysis results in chemical consumption of the hydrogen fluoride and the formation of peracylated carbohydrates.

4. The method of claim 1, wherein the step of terminating the solvolysis involves reacting the depolymerized carbohydrate in the hydrogen fluoride with at least an equimolar quantity of a carboxylic acid anhydride, based on the molar quantity of hydrogen fluoride.

5. The method of claim 1, wherein the carboxylic acid anhydride comprises acetic anhydride.

6. The method of claim 1, wherein prior to terminating the solvolysis, at least one of the carboxylic acid anhydride and the polymeric carbohydrate in hydrogen fluoride is cooled to a temperature of at least 0° C.

7. The method of claim 3, further comprising, after terminating the solvolysis and prior to quantifying the peracylated carbohydrates, drying the peracylated carbohydrates to evaporate reaction byproducts.

8. The method of claim 7, wherein the step of quantifying the peracylated carbohydrates involves analysis of the peracylated carbohydrates using a gas chromatograph.

9. The method of claim 8, wherein the eluent from the gas chromatograph is analyzed using a mass spectrometer.

10. The method of claim 1, further comprising, after the step of solvolyzing and before the step of terminating the solvolysis, the addition of methanol to the depolymerized carbohydrate in the hydrogen fluoride, thereby forming methyl glycosides.

11. The method of claim 1, wherein the step of terminating the solvolysis further comprises reacting the carboxylic acid anhydride with the depolymerized carbohydrate in hydrogen fluoride, followed by warming the resulting reaction mixture to an above ambient temperature to encourage the formation of pentaacetate carbohydrates.

12. The method of claim 11, wherein the carboxylic acid anhydride and depolymerized carbohydrate in hydrogen fluoride reaction mixture is heated to a temperature of approximately 80° C.

13. The method of claim 1, further comprising, after the step of solvolyzing and prior to the step of terminating solvolysis, reacting a quantity of acetic acid, based on the molar quantity of hydrogen fluoride, with the depolymerized carbohydrate in hydrogen fluoride, followed by warming the resulting reaction mixture to an above ambient temperature, wherein the step of terminating the solvolysis comprises reacting an excess of a carboxylic acid anhydride with the reaction mixture, thereby encouraging the formation of pentaacetate carbohydrate derivatives.

14. The method of claim 13, wherein the acetic acid and depolymerized carbohydrate in hydrogen fluoride reaction mixture is heated to a temperature of approximately 80° C.

15. A method for preparing polymeric carbohydrates for qualitative or quantitative analysis, comprising the steps of:
    (a) solvolyzing a polymeric carbohydrate in anhydrous hydrogen fluoride to yield a solution of at least partially depolymerized carbohydrate;
    (b) terminating the solvolysis by reacting the solution of at least partially depolymerized carbohydrate in the hydrogen fluoride with a carboxylic acid anhydride, thereby chemically consuming the hydrogen fluoride by forming acetic acid(,) and acetyl fluoride, the acetyl fluoride then acting to derivatize the depolymerized carbohydrate by forming peracylated carbohydrates; and (c) evaporating off the acetyl fluoride, the acetic acid and any remaining carboxylic acid anhydride from the peracylated carbohydrates.

16. The method claim 15, wherein the step of solvolyzing includes controlling the temperature of the polymeric carbohydrate and hydrogen fluoride during solvolysis at a selected temperature of from −20° to 20° C.

17. The method of claim 15, wherein the step of terminating the solvolysis involves reacting the depolymerized carbohydrate in the hydrogen fluoride with at least an equimolar quantity of a carboxylic acid anhydride, based on the molar quantity of hydrogen fluoride.

18. The method of claim 15, wherein the carboxylic acid anhydride comprises acetic anhydride.

19. The method of claim 15, further comprising, after the step of solvolyzing and before the step of terminating the solvolysis, the addition of methanol to the depolymerized carbohydrate in the hydrogen fluoride, thereby forming methyl glycosides.

20. The method of claim 15, wherein during the step of terminating the solvolysis comprises reacting a carboxylic acid anhydride with the depolymerized carbohydrate in hydrogen fluoride, followed by warming the resulting reaction mixture to an above ambient temperature to encourage the formation of pentaacetate carbohydrates.

21. The method of claim 20, wherein the carboxylic acid anhydride and depolymerized carbohydrate in hydrogen fluoride reaction mixture is heated to a temperature of approximately 80° C.

22. The method of claim 15, further comprising, after the step of solvolyzing and prior to the step of terminating solvolysis, reacting an equimolar quantity of acetic acid, based on the molar quantity of hydrogen fluoride, with the depolymerized carbohydrate in hydrogen fluoride, followed by warming the resulting reaction mixture to an above ambient temperature, wherein the step of terminating the solvolysis comprises reacting an excess of the carboxylic acid anhydride with the reaction mixture, thereby encouraging the formation of pentaacetate carbohydrate derivatives.

23. The method of claim 22, wherein the acetic acid and depolymerized carbohydrate in hydrogen fluoride reaction mixture is heated to a temperature of approximately 80° C.

24. The method of claim 1, wherein the step of solvolyzing further comprises solvolyzing an unprotected polymeric carbohydrate.

25. The method of claim 1, wherein the step of solvolyzing further comprises solvolyzing the polymeric carbohydrate in substantially pure anhydrous hydrogen fluoride.

* * * * *

UNITED STATES PATENT AND TRADEMARK OFFICE
CERTIFICATE OF CORRECTION

PATENT NO. : 5,411,892
DATED : May 2, 1995
INVENTOR(S) : B.A. Mergamaschi

It is certified that error appears in the above-indentified patent and that said Letters Patent is hereby corrected as shown below:

| COLUMN | LINE | |
|---|---|---|
| 2 | 64 | "(ii)followed" should read --(ii) followed)-- |
| 2 | 67 | "arthydride" should read --anhydride-- |
| 3 | 6 | "sololysis" should read --solvolysis-- |
| 4 | 30 | "tbur" should read --four-- |
| 4 | 67-68 | "arthydride" should read --anhydride-- |
| 5 | 4 | "arthydride" should read --anhydride-- |
| 5 | 27 | "tier" should read --for-- |
| 6 | 47 | "tier" should read --for-- |
| 6 | 51 | "For" should read --for-- |
| 7 | 57 | "tile" should read --the-- |
| 9 | 9 | "tile" should read --the-- |

UNITED STATES PATENT AND TRADEMARK OFFICE
CERTIFICATE OF CORRECTION

PATENT NO. : 5,411,892
DATED : May 2, 1995
INVENTOR(S) : B.A. Mergamaschi

It is certified that error appears in the above-indentified patent and that said Letters Patent is hereby corrected as shown below:

| | | |
|---|---|---|
| 9-10 | 68-1 | "70 Evionization" should read --70 Ev ioniation-- |
| 11 | 12 | "redtying" should read --redrying-- |
| 11 | 46 | "original)" should read --ordinary-- |

Signed and Sealed this

Third Day of October, 1995

Attest:

BRUCE LEHMAN

Attesting Officer     Commissioner of Patents and Trademarks